United States Patent [19]

Mulreany et al.

[11] Patent Number: 4,838,856
[45] Date of Patent: Jun. 13, 1989

[54] FLUID INFUSION FLOW CONTROL SYSTEM

[75] Inventors: Patrick A. Mulreany, Wellington, Nev.; Alan C. Kinney, Auberry, Calif.; Donald C. Presley, Sparks, Nev.

[73] Assignee: Truckee Meadows Research & Development, Sparks, Nev.

[21] Appl. No.: 70,819

[22] Filed: Jul. 2, 1987

[51] Int. Cl.[4] ............................................. A61M 5/16
[52] U.S. Cl. ...................................... 604/65; 604/67; 604/52; 604/81; 128/DIG. 13
[58] Field of Search ..................... 73/239-240, 73/249, 252; 604/50, 65-67, 80-81, 245; 128/DIG. 12-13; 417/3-4, 412

[56] References Cited

U.S. PATENT DOCUMENTS

| | | | |
|---|---|---|---|
| 3,344,667 | 10/1967 | Maltby | 73/239 |
| 3,657,925 | 4/1972 | Gross | 73/239 |
| 4,191,184 | 3/1980 | Carlisle | 604/153 |
| 4,207,871 | 6/1980 | Jenkins | 604/65 |
| 4,240,291 | 12/1980 | Andersson et al. | 73/239 X |
| 4,308,866 | 1/1982 | Jelliffe et al. | 604/67 X |
| 4,384,578 | 5/1983 | Winkler | 604/151 X |
| 4,468,219 | 8/1984 | George et al. | 604/67 X |
| 4,553,958 | 11/1985 | LeCocq | 604/67 |
| 4,613,325 | 9/1986 | Abrams | 604/65 |
| 4,681,563 | 7/1987 | Deckert et al. | 604/67 |
| 4,690,673 | 9/1987 | Bloomquist | 604/67 |

Primary Examiner—Francis Jaworski
Attorney, Agent, or Firm—Fleit, Jacobson, Cohn & Price

[57] ABSTRACT

Flow of fluid from primary and secondary reservoirs is induced along parallel flow paths to a common infusion device under gravity or pump inducing modes, respectively. The fluid delivered to the infusion device is monitored by a flow meter to measure its actual flow rate and adjust flow along the parallel flow paths to maintain a substantially constant selected flow rate by means of a programmed control system through which selection of the flow inducing mode and the reservoir may be effected.

14 Claims, 10 Drawing Sheets

FLUID INFUSION FLOW CONTROL SYSTEM

BACKGROUND OF THE INVENTION

This invention relates generally to control of the flow of fluids, such as fluids intravenously infused into medical patients.

The infusion of intravenous fluid requires precise control over the volume of fluid infused and the infusion flow rate in accordance with preselected values and different types of flow controlling devices have heretofore been utilized to meet the relatively wide variation of flow requirements. The flow of fluid through such prior flow controlling devices is induced by two basic methods, one being a gravity feed method and the other a positive fluid displacement pump method.

The gravity feed type of flow controller is associated with a drip counting method of monitoring flow. Because of the variables involved, such as fluid viscosity, this type of flow controller is of limited use and subject to errors in the determination of flow rate data from which flow control may be exercised.

In an effort to obtain more precise flow control, particularly where fluid is to be administered at relatively higher infusion flow rates beyond the capability of gravity feed controllers, the pump induced flow type of controller is utilized. Many of the latter type of flow controller utilize a peristaltic pump to avoid the severe pulsation effects of piston pumps and the complex and costly valve systems required to cope therewith. However, the peristaltic pumps also have certain drawbacks, such as unsteady flow rate making them unsuitable for delivery of fluid at low flow rates in spite of valving systems devised to cope with the unsteady flow characteristics.

In general, flow controllers utilizing peristaltic pumps have been devised in cassette form, having access doors and front panels mounting membrane key pads, operational status indicators, readout data displays and alarm devices. Such cassettes encompass flow meters as well as other expedients generally known in the art, such as cassette code identifying detectors, malfunction sensors, etc.

As a result of the aforementioned drawbacks associated with known flow controllers, it has been necessary to sometimes change the type of flow controller deemed desirable for intravenous administration, with a consequential interruption in fluid infusion to the patient. Further, because of the difficulties encountered in measuring both low and high flow rates, the flow meter has been eliminated from some flow controllers because of costs and lack of reliability. Additionally, prior flow controllers were unable to provide for rapid change in the source of fluid, between primary and secondary reservoirs, for example.

It is, therefore, an important object of the present invention to provide an infusion flow controller system through which flow of the fluid may be induced from selected reservoirs alternatively by gravity feed and pump displacement through operational mode selection without any installational change.

Another object in accordance with the foregoing object is to provide the infusion flow controller system with a flow meter capable of monitoring flow under either operational mode to provide accurate flow volume and rate data for display and for flow adjustment so as to achieve steady flow conditions.

Other objects in association with the foregoing objects include the detection of errors, malfunctions and the monitoring of operational modes peculiar to the unique attributes of the infusion flow controller system of the present invention.

SUMMARY OF THE INVENTION

The infusion flow controller system of the present invention withdraws fluid from standard bottle or bag reservoirs for alternative or simultaneous flow along two parallel paths under gravity and pump inducement, respectively, in accordance with operator mode selection thereby remedying the aforementioned drawbacks associated with flow controllers limited to either gravity feed or positive pump displacement. The flow of the fluid so induced is conducted through a flow meter to a common infusion device. The flow meter is programmed to cyclically displace a fixed volume of the fluid at a rate of movement dependent on the actual volumetric flow rate of the fluid being delivered. Accurate flow rate measurements are thereby obtained by an image position sensor detecting the travel limits of a fluid displacing piston in the flow meter and monitoring cyclically reversing movement of the piston between such limits to provide operational data and adjust flow along the parallel flow paths through flow valve control and pump control, respectively. The outputs of the flow meter sensor are accordingly fed to a data processing system through which readout to status indicators and a data display is provided as well as program control of the flow meter operation and flow adjustment of the gravity feed, flow control valve and the pump speed.

According to one embodiment of the invention, a cassette incorporates a peristaltic type pump together with the flow control valve, the flow meter, over-pressure sensor, cassette code identifier, gravity feed selection valves, flow shut-off valve and an air-in-line sensor. The data processing control system may be housed in common with the removable cassette within an instrument housing and is interfaced therewith through the sensors and detectors and through electronic valve and pump control circuits. The housing supports a panel mounting a membrane type of key pad through which the operator enters coded inputs to the data processing control system for selection of reservoirs, selection of flow inducing mode of operation, selection of flow rate and fluid volume to be infused as well as other control functions. The panel also mounts a display for readout of information from the data processing control system relating to diagnostic information and status indicators through which data on operational conditions are read out.

BRIEF DESCRIPTION OF DRAWING FIGURES

The foregoing objects, features and advantages of the invention, as well as others, will become apparent from the following detailed description given by way of example to be read in connection with the accompanying drawings, wherein.

DETAILED DESCRIPTION OF PREFERRED EMBODIMENT

Figure 1:
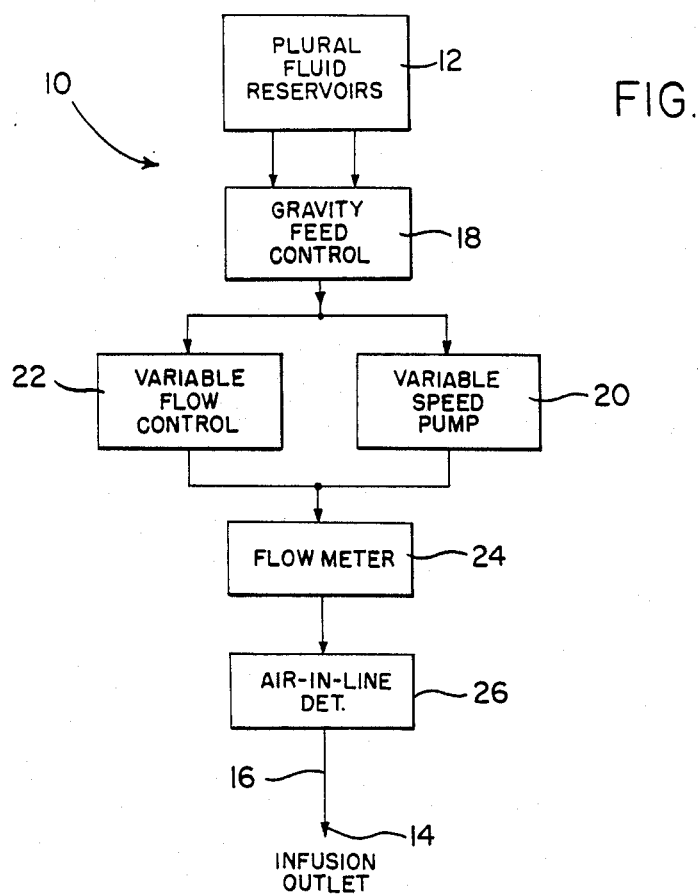
FIG. 1 is a schematic block diagram depicting the infusion flow control system of the present invention.

Referring now to the drawings in detail, FIG. 1 schematically illustrates an infusion control system generally referred to by reference numeral 10 through which fluid from a source 12 formed by a plurality of reservoirs, is delivered to a patient through an infusion outlet 14 such as an intravenous needle connected to an outlet conduit segment 16. The fluid originating from the reservoir source 12, is conducted through a feed control section 18 to two parallel flow paths established through a variable speed pump 20 of the peristaltic type and a variable flow control section 22. The flow of fluid through either one of the parallel paths under exclusive gravity inducement or positive pump displacement, or through both of said paths in accordance with other operational modes, is conducted through a flow meter 24 to the infusion outlet conduit section 16. An air-in-line detector 26 is operatively placed in the flow path between the outlet side of the flow meter 24 and the outlet conduit section 16.

Figure 2A:
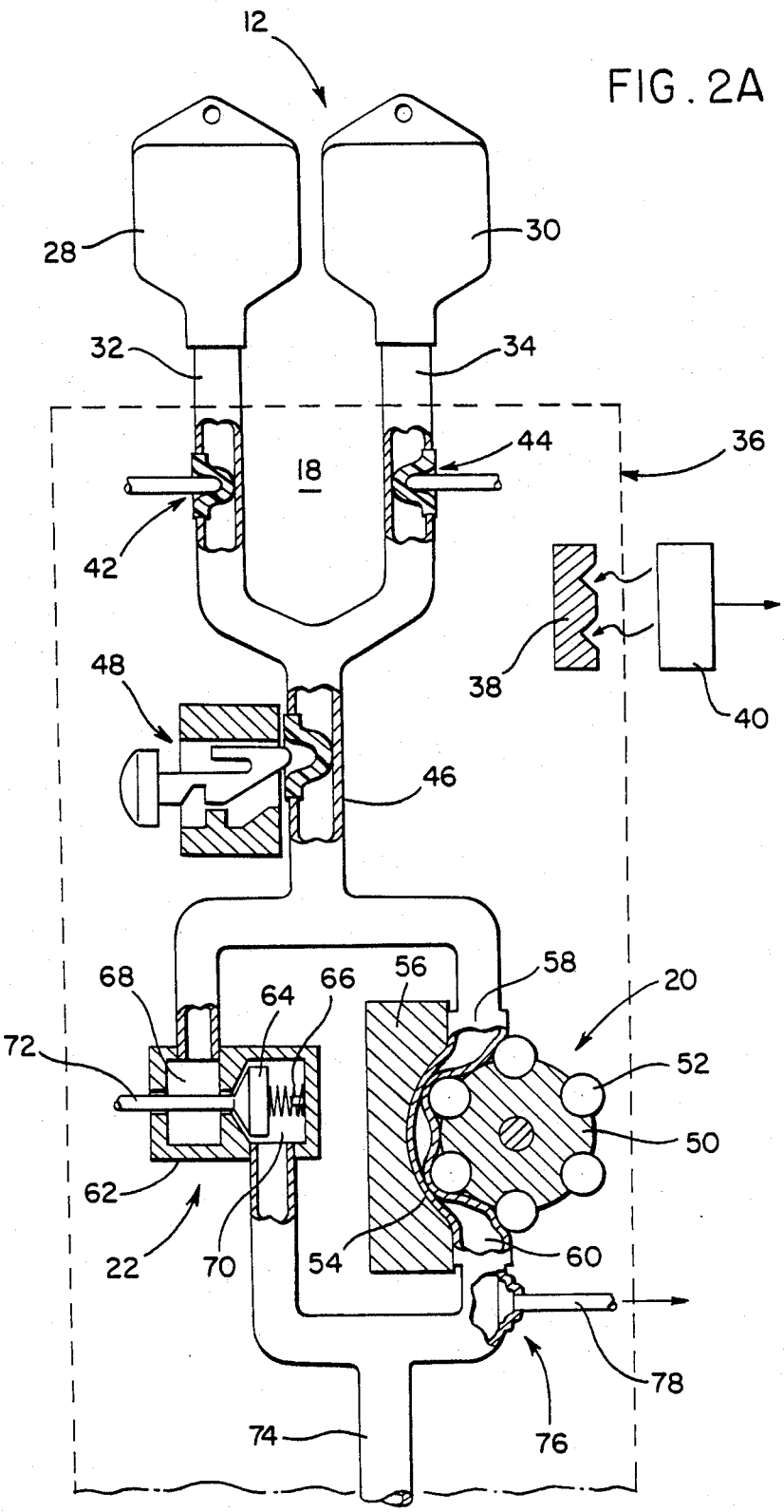
FIGS. 2A and 2B are somewhat simplified elevation views of the hardware associated with the control system depicted in FIG. 1, with parts shown in section.
Figure 2B:
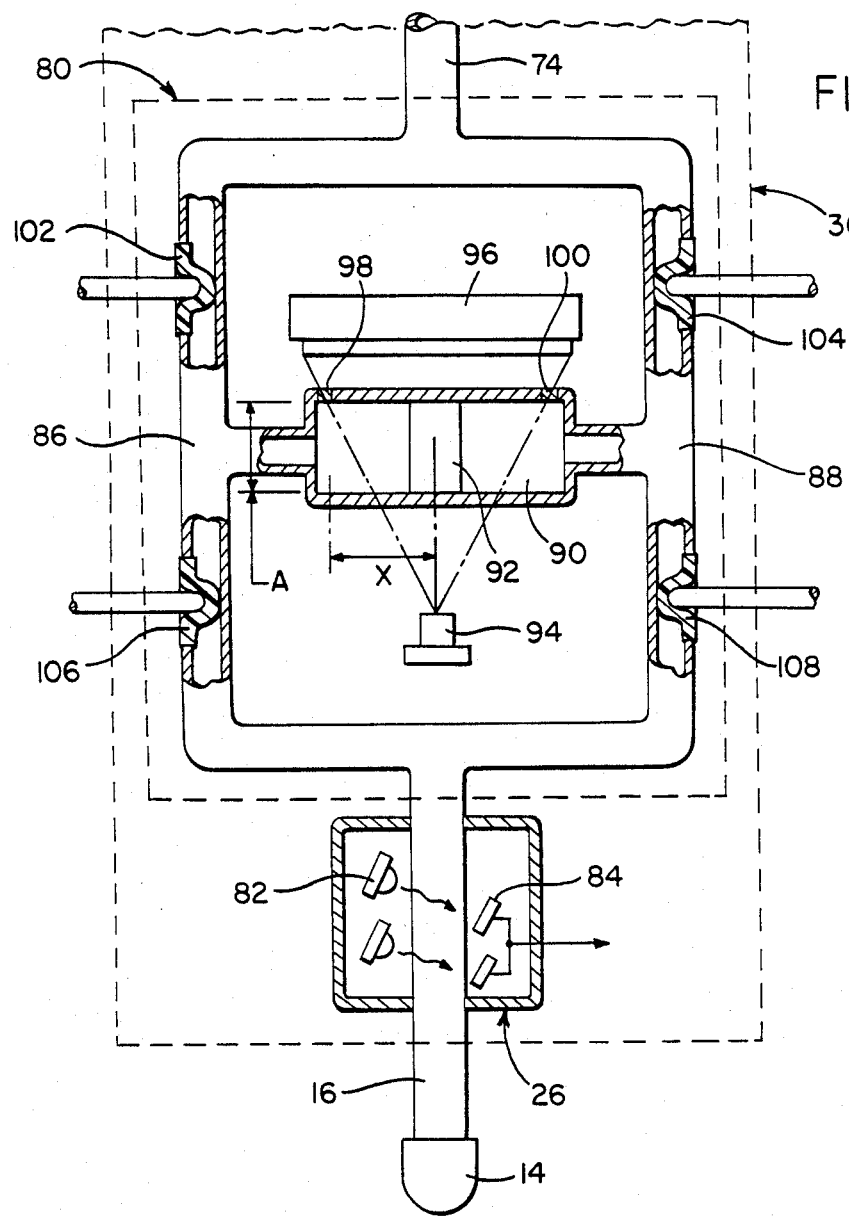

FIGS. 2A and 2B illustrate in greater detail one embodiment of the apparatus associated with the system depicted in FIG. 1. The fluid reservoir source 12 as shown in FIG. 2A, is established by at least two standard (IV) bag reservoirs 28 and 30 respectively connected by primary feed tube 32 and secondary feed tube 34 to the infusion flow control system which may be embodied in a removable cassette structure, generally referred to by reference numeral 36, of a type already generally known in the art. The cassette structure may have associated therewith a cassette identifying code structure 38 adapted to be sensed by an electronic detector 40 when the cassette is inserted into an instrument housing in a manner generally well known in the art. The reservoir feed control section 18 is formed by a pair of valve devices 42 and 44 incorporated into the cassette for respectively closing and opening the primary and secondary feed tubes 32 and 34. The feed tubes are interconnected with a common supply tube 46 to which a flow cut-off valve 48 is connected. The flow cut-off valve 48 is operative to maintain the supply tube 46 closed thereby preventing the flow of fluid from the reservoirs while the cassette 36 is withdrawn from its installation. When the cassette is properly inserted into its housing structure, the valve 48 opens to permit the flow of fluid from one of the reservoirs 28 and 30 to the flow controlling pump 20 and the flow control section 22 aforementioned in connection with FIG. 1.

The peristaltic pump 20, which is generally well known in the art, includes a rotor 50 peripherally mounting circumferentially spaced rollers 52 adapted to engage flexible tubing 54 backed along an arcuate path by a fixed track structure 56 as shown. As will be understood by persons skilled in the art, fluid is displaced through the flexible tubing 54 in response to rotation of the pump rotor 50 causing angular movement of the tube constricting rollers 52 which thereby displace fluid trapped in the tubing 54 between the rollers. Fluid is thereby displaced between the inlet and outlet ends 58 and 60 of the pump under a positive pump pressure at a volumetric flow rate dependent on the rotational speed of the pump rotor 50.

Fluid from the reservoir source is also conducted in parallel, bypass relation to the pump 20 through the variable flow control section 22 aforementioned in connection with FIG. 1. As shown in FIG. 2A, the flow control section 22 includes a valve housing 62 within which a slidable valve element 64 is mounted biased by spring 66 to a closed position engaging a conical valve seat separating inlet and outlet chambers 68 and 70. A valve actuator 72 extends from the valve element 64 in order to effect displacement of the valve element from its closed position against the bias of spring 66 by varying amounts to control the flow of fluid therethrough at an adjusted flow rate. Fluid conducted through either of the parallel paths is fed by a tube section 74 to the flow meter 24. The pressure of the fluid in the tube section 74 is, however, monitored by an over-pressure sensor 76 which may be in the form of a flexible diaphragm to which a signal transmitting rod element 78 is connected.

The flow meter 24 as shown in FIG. 2B, may form a separate module 80 interconnected between the tube section 74 and 16 within cassette 36. The air-in-line detector 26 aforementioned in connection with FIG. 1, is schematically shown in FIG. 2B located between the flow meter module 80 and the infusion outlet conduit section 16. The detector 26 may be of the type in which radiation from sources 82 is emitted and transmitted through the fluid in the conduit section 16. Any air bubbles in the fluid will accordingly be sensed by radiation detectors 84 from which a signal is derived to indicate the presence of air in the fluid.

With continued reference to FIG. 2B, the flow meter 24 conducts fluid between the supply conduit 74 and the infusion outlet conduit section 16 along parallel tubing sections 86 and 88. Intermediate portions of the tubing sections 86 and 88 are interconnected with opposite axial ends of a pressure sealed tubular chamber 90 within which a piston element 92 is displaceable between travel limit positions adjacent the opposite axial ends of the chamber. The tubular chamber 90 according to one embodiment is made of a radiation transmissive material whereas the piston element 92 is made of alternate bands of an opaque material blocking the transmission of light and transmissive bands through which light or radiation passes. The radiation is emitted from a lamp source 94 spaced on one side of the tubular chamber 90 opposite an image sensing array 96. According to one embodiment of the invention, the image sensor 96 may be of an optical character recognition type utilized in facsimile equipment. Such sensors consist of a linear array of photo sensitive cells and the necessary circuitry to transfer position data with respect to the piston element 92 in the form of electrical charge information from the photo cell sites. It should, of course, be appreciated that other types of image sensing devices may be utilized. In the present case, the sensor 96 furnishes information regarding the instantaneous positions of the piston element 92 between travel limit positions detected by the sensor upon blockage of the radiation at travel limit locations 98 and 100 corresponding to the end of travel of the piston element.

Pressurized fluid from the fluid source is conducted along two alternate paths within the flow meter through tubing sections 86 and 88 under control of a pair of flow directing in-flow valves 102 and 104. Accordingly, with one of the in-flow directing valves 102 and 104 closed and the other open, pressurized fluid will enter the tubular chamber 90 at one axial end causing the piston element 92 to be displaced in one axial direction toward one of its limit positions during a measurement cycle. Fluid occupying the tubular chamber 90 on one side of the piston element from a previous measurement cycle will accordingly be displaced by the piston element into tubing section 86 or 88 depending upon which of two out-flow directing valves 106 and 108 is closed. The piston element 92 will thereby displace a quantity of fluid for discharge into the infusion outlet conduit section 16 through the open out-flow directing valve 106 or 108 in the tube sections 86 and 88 downstream of the valves 102 and 104. Thus, during each measurement cycle of the flow meter 24, a measured quantity of fluid will be displaced at a rate dependent upon the flow of fluid to the flow meter from tube section 74, provided the flow directing valves 102, 104, 106 and 108 are cyclically opened and closed in proper operational relationship to the movement of the piston element 92 between its travel limit positions. For example, during travel of the piston element 92 in a right hand direction as viewed in FIG. 2B, valve 102 will be open to conduct pressurized fluid into the chamber 90 at its left end while valve 104 is closed. Fluid will accordingly be displaced by the piston element 92 from the chamber 90 and flow toward the outlet conduit section 16 through valve 108 which is then opened, valve 106 being closed. When the piston element 92 reaches its travel limit position blocking transmission of light through location 100, a travel limit signal from the image sensor 96 will cause valves 104 and 106 to open while closing valves 102 and 108. Such resulting change in the in-flow and out-flow paths of fluid relative to the chamber 90 will cause the piston element 92 to reverse its travel direction and begin another measurement cycle. The duration of the measurement cycles will, of course, vary in dependence on the in-flow rate of the fluid as aforementioned. The position sensing output of the sensor 96 with respect to time will, therefore, provide a volumetric flow rate measurement in an accurate and reliable manner. Such operation of the flow meter 24 will, of course, require programmed control of the valves 102, 104, 106 and 108 as aforementioned and detection of the travel limits to provide the volumetric flow rate measurement information.

Figure 3:
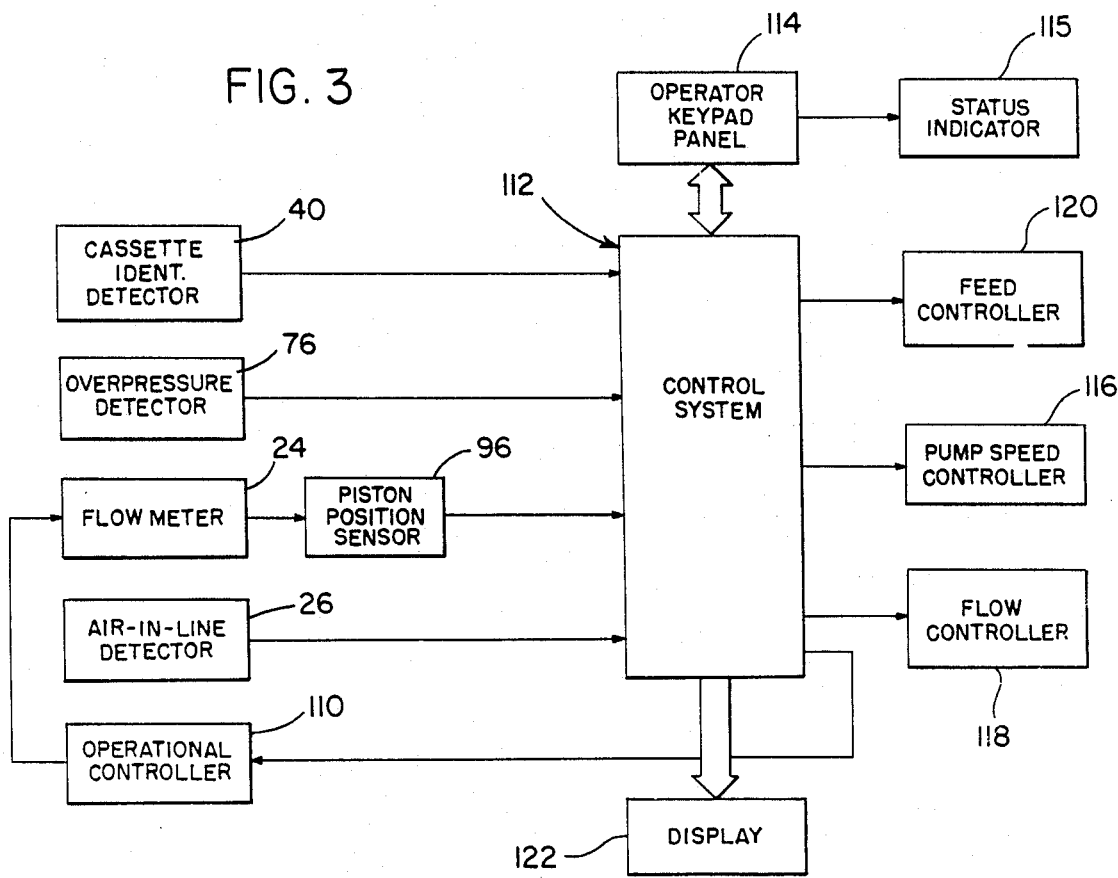
FIG. 3 is a block diagram schematically illustrating the data processing control system associated with the apparatus of the present invention.

As diagramed in FIG. 3, control of the flow directing valves of the flow meter 24 is effected through an operational valve controller 110 receiving its command signals from a programmed data processing control system generally referred to by reference number 112. Programmed control of the flow directing valves as aforementioned, is triggered by signals from the sensor 96 in response to detection of the piston element reaching its travel limits. Such sensor output signals are fed to the data processing control system as shown in FIG. 3. The output of the sensor 96 also supplies the flow rate measurement information to the data processing system by means of which a preselected flow rate for the infusion of fluid is established. Selection of the operational mode and the flow rate is achieved through an operator input key pad 114 interfaced with the data processing system. In order to maintain the preselected volumetric flow rate, the speed of the pump 20, is adjusted to meet various needs such as extension of the flow rate range of the pump, fine tuning of its flow control, venting pump overpressure during start-up and smoothing out pump flow rate pulsations, by way of example. Such adjustments are effected or the opening of the flow control valve 22 is adjusted through a pump speed controller 116 or a flow controller 118 respectively interfacing the pump 20 and flow control 22 with the data processing system as diagrammed in FIG. 3. The input key pad 114 associated with the data processing system will not only enable selection of mode and flow rate but also provides other control functions such as the selection of the fluid reservoir from which the infusion fluid is to be withdrawn. Toward that end, a feed controller 120 interfaces the data processing system with the aforementioned valves 42 and 44 of the gravity feed control section 18. Thus, the operator by means of an appropriate coded input to the data processing control system may select one or both of the reservoirs for the source of fluid.

Information is also fed to the data processing control system 112 from the air-in-line detector 26 and the cassette identifying detector 40 aforementioned in connection with FIGS. 2A and 2B. The data processing control system will accordingly respond to various alarm conditions such as over-pressure in order to stop flow of fluid as well as to display alarm conditions and institute a visual and/or audible alarm through a display section 122 as diagramed in FIG. 3 and indicate operational status through an indicator 115 associated with the panel on which the key pad 114 is mounted.

Figure 4:
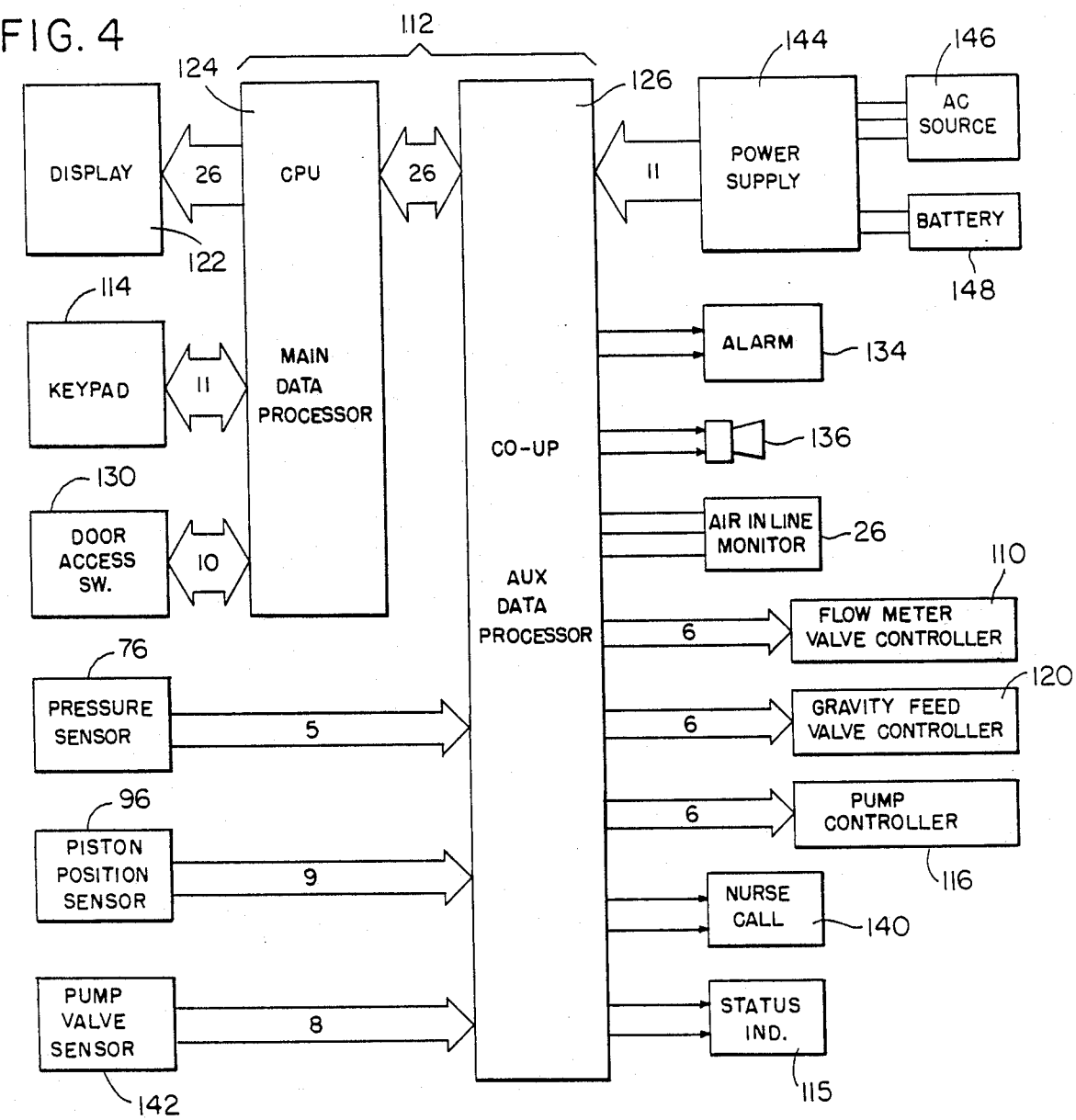
FIG. 4 is a block diagram illustrating interconnections between components of the data processing system.

In accordance with one embodiment of the invention as schematically depicted in FIG. 4, the data processing control system 112 includes a main data processor 124 interfaced with an auxiliary data processor 126. The main data processor controls readout of information to the visual display 122 when conditioned for operation by the operator through key pad 114 and a door access switch 130. The over-pressure sensor 76 and the piston position sensor 96 associated with the flow meter, feed information to the auxiliary data processor 126 from which outputs are derived for the display 122 as well as a visual alarm 134, an audible alarm 136, the status indicator 115 and a nurse call device 140. The pump speed controller 116, the flow controller 118 and the reservoir feed controller 120 also receives command signals from the auxiliary data processor 126 as shown. Additionally, a valve sensor 142 provides feedback information to the auxiliary data processor 126 from the flow meter 24. Power for operating the control system is derived from a power supply 144, as diagramed in FIG. 4, interfaced with the auxiliary data processor 126. The power supply section is connected to an available AC power source 146 and to a battery source of electrical energy 148.

With continued reference to FIG. 4, the main data processor 124 receives input data from the operator through the key pad 114 adapted to be mounted on a front panel with the status indicator 115. Operation of the status indicator will be controlled by signals generated in the main data processor 124 which also generates messages for display and performs various calculating functions including determination of the volume of fluid delivered, the remaining infusion time and fluid flow rate. Also, the main data processor 124 determines the existence of error conditions.

The auxiliary data processor 126 as diagrammed in FIG. 4 is interfaced with the main data processor 124 and programmed to perform various functions including the generation of control signals for the pump speed controller 116, the selection of reservoir feed through the feed controller 120, and the generation of control signals for the flow meter valves through the valve controller 110. The auxiliary data processor 126 will process fluid delivery data received from the flow meter by means of the sensor 96 and will generate control signals for the various analog data measurements to be made.

By means of data processing techniques generally known in the art, the main and auxiliary data processors 124 and 126 intercommunicate through their interfacing to read out information through display 122 relating to infusion time remaining, flow tube occlusion, air-in-line, fluid volume delivered, flow delivery rate and infusion completed. The status indicator section 115 on the other hand, will provide readout information on operational conditions including but not necessarily limited to selected volume to be infused, flow rate selection, mode selection, hold, alarm reset, run, clear, access door open, KVO operation and battery condition.

Figure 5:
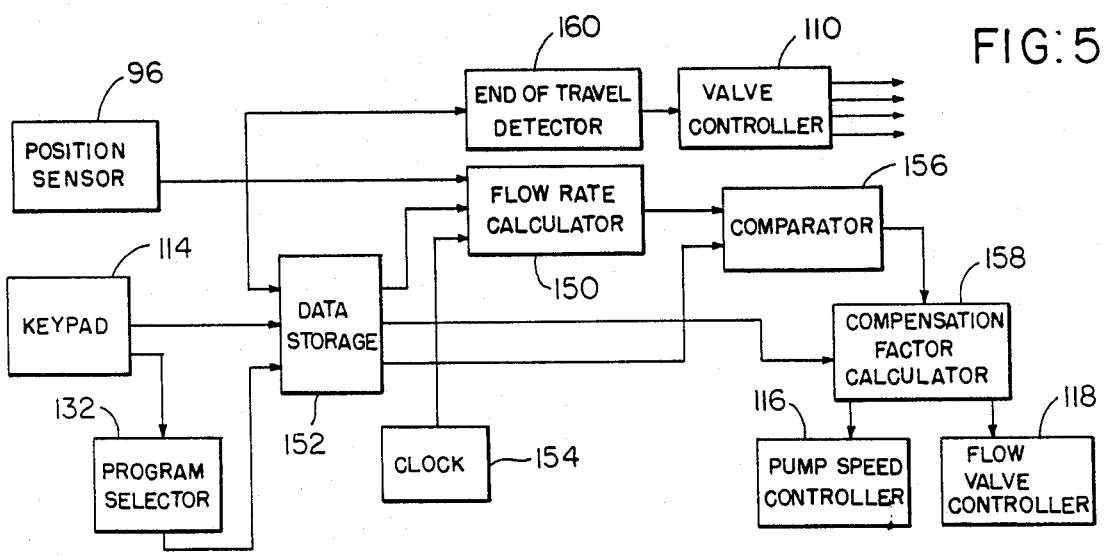
FIG. 5 is a functional block diagram relating to programmed operation of the flow meter associated with the infusion flow control system of the present invention.

FIG. 5 is a block diagram functionally depicting the programmed operation of the flow meter 24 through the control system 112 as hereinbefore described. As shown, the input from the position sensor 96 associated with the flow meter is fed to a flow rate calculating section 150 which also receives input data from a data storage 152 and timing information from a system clock 154. Thus, a flow rate output is obtained from the calculator 150 which is a function of the volumetric measurement data supplied thereto from the position sensor 96. The measurement flow rate data is compared with a preselected, storage flow rate value from the data storage 152 within a comparator section 156. Any differential between the flow rate measurement and the preselected flow rate will accordingly be fed by the comparator 156 to a compensation factor calculator 158 from which command signals are fed to the pump speed controller 116 or the flow controller 118 to effect the dynamic flow rate adjustments aforementioned. The compensation factor calculator generates the command signals as a function of the differential output of the comparator 156 and the data received from storage 152. The data storage will accordingly read out information to the calculator 158 in response to inputs from the operator key pad 114 relating to preselected flow rate and mode selection and from an initial measurement output of the position sensor 96. The mode selection from the key pad 114 is effected through a program selector 132. Travel limit information from the output of the position sensor 96 is detected by an end of travel detector 160 for programmed control of the flow directing valve controller 110 which operates the flow directing valves of the flow meter as aforementioned in connection with FIG. 2B.

Figure 6A:
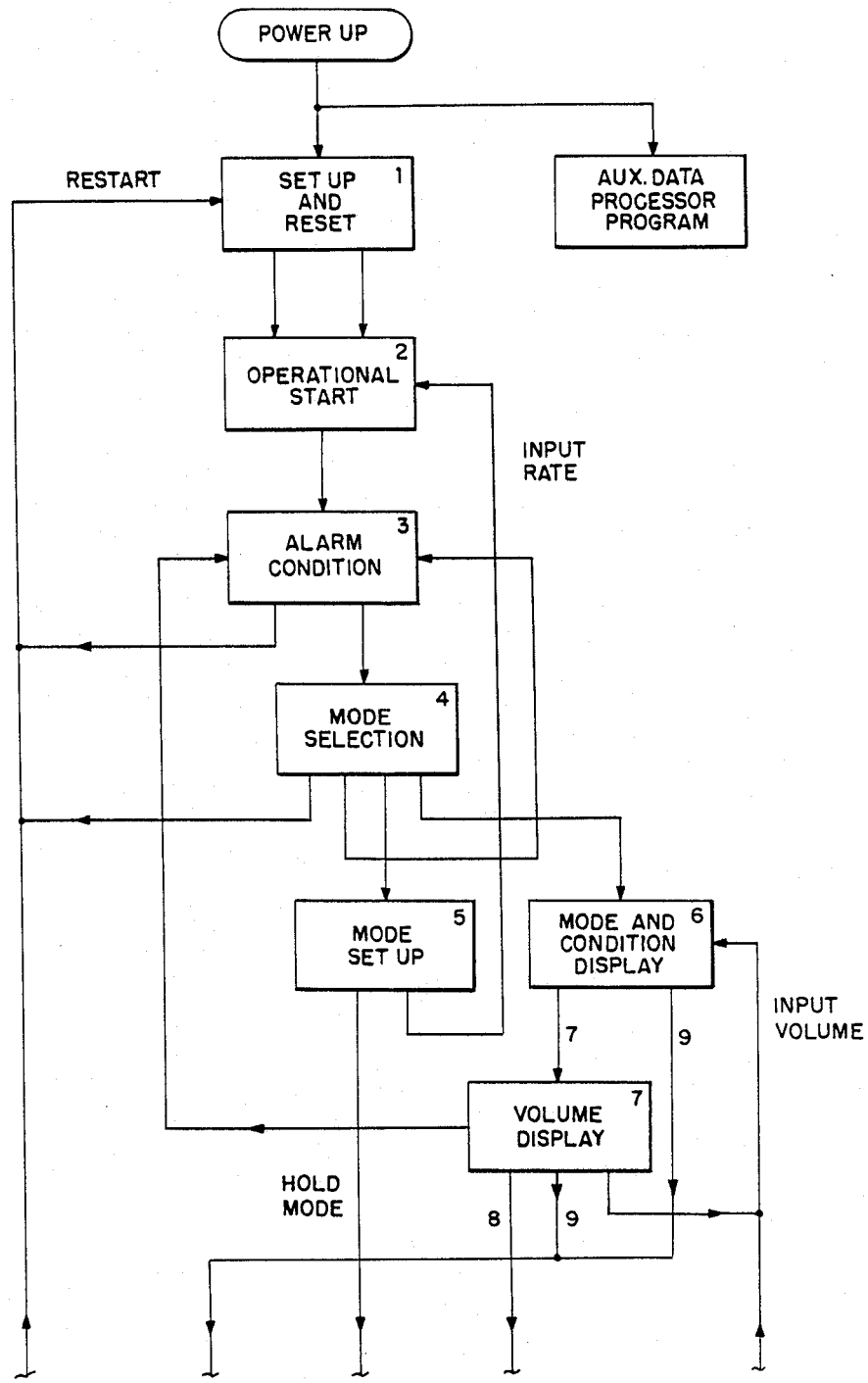
FIGS. 6A and 6B are program flow charts relating to programmed operation of the main data processor associated with the electronic control system.
Figure 6B:
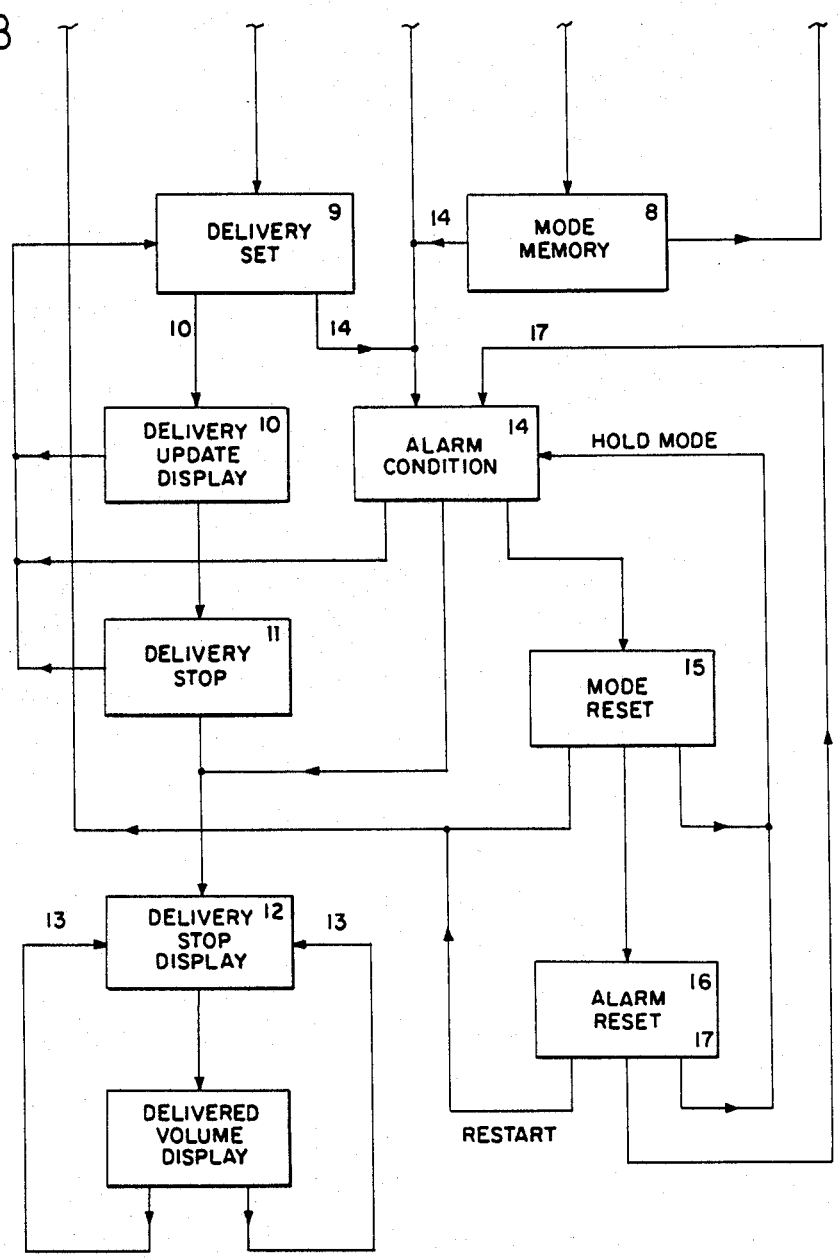
Figure 7:
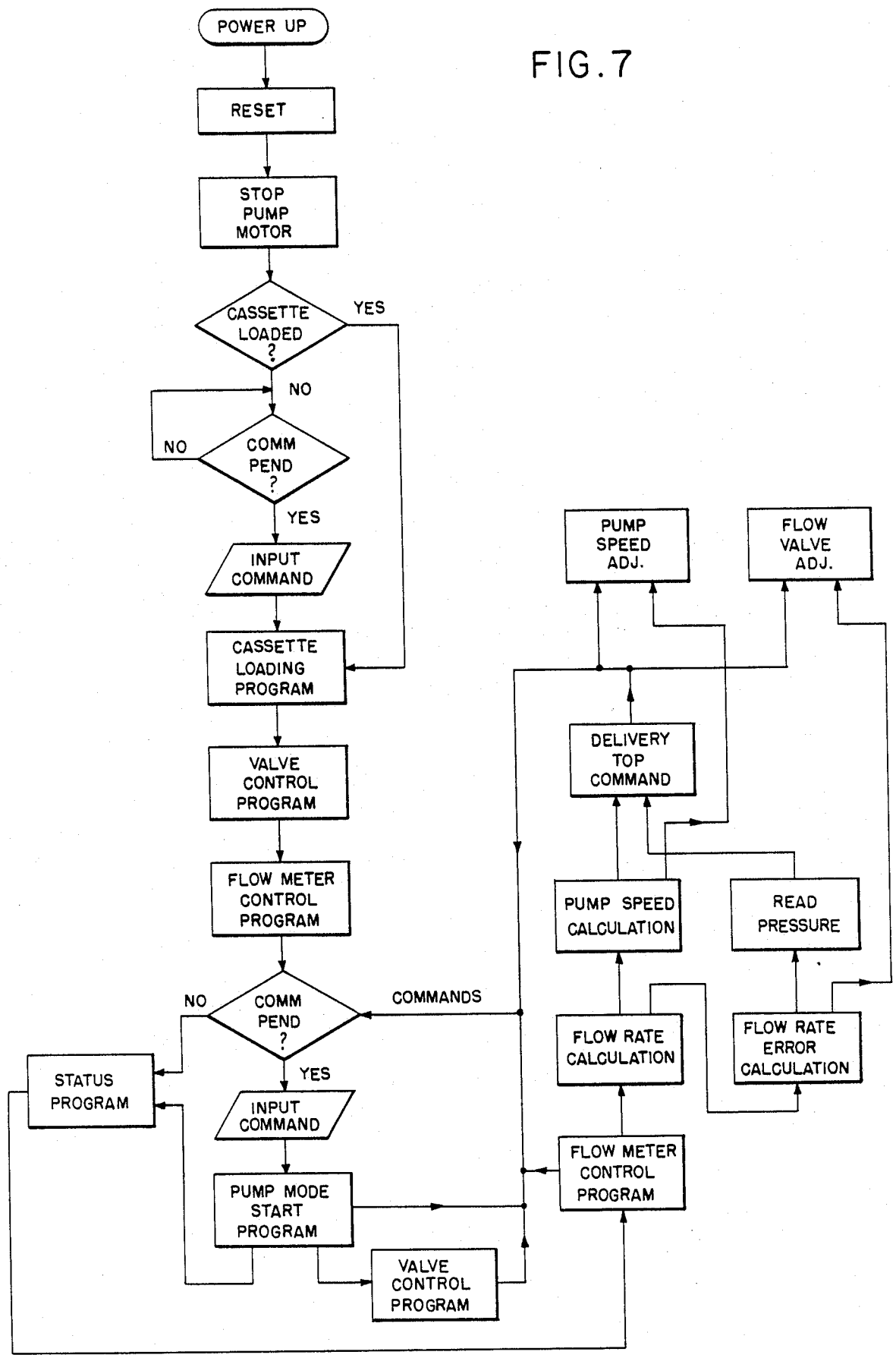
FIG. 7 is a program flow chart relating to programmed operation of the auxiliary data processor associated with the electronic control system.

The foregoing flow meter control program as described with respect to FIG. 5, is incorporated within the operational program associated with the auxiliary data processor 126 performing the other functions aforementioned as diagramed in the program flow chart of FIG. 7 while the operational program for the main data processor 124 is diagrammed in the program flow chart of FIGS. 6A and 6B containing self-explanatory labels.

Figure 8:
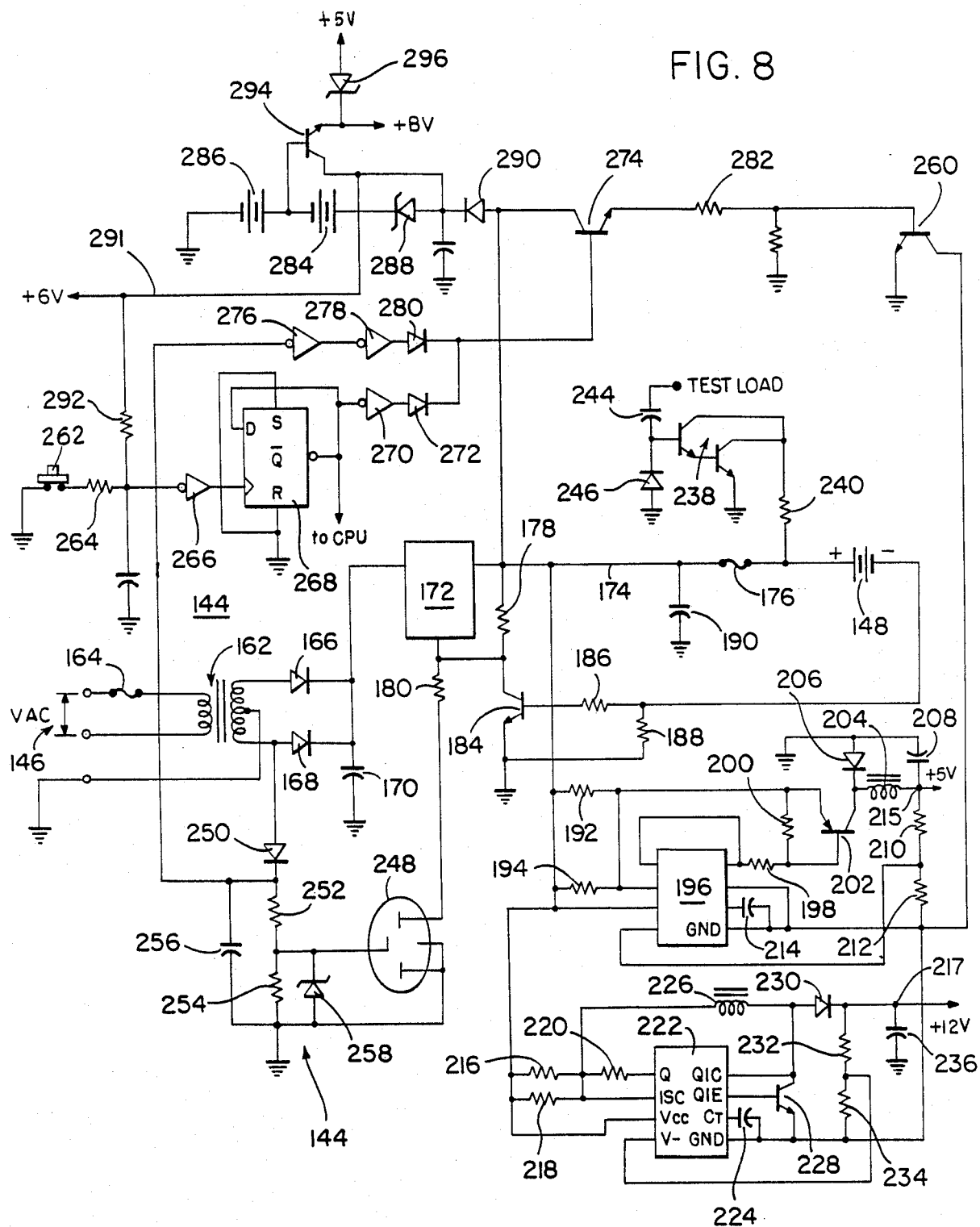
FIG. 8 is an electrical circuit diagram illustrating in detail the power supplies associated with the electronic control system as diagrammed in FIG. 4.

According to one embodiment of the invention as depicted in FIG. 8, the power supply section 144 hereinbefore referred to in connection with FIG. 4, includes a main power transformer 162 connected to the AC power source 146 through a main AC line fuse 164. The AC output of the transformer 162 is rectified by diodes 166 and 168, and filtered by a capacitor 170. Accordingly, a rectified and filtered DC voltage is supplied to a current and voltage regulator 172 for a main battery bus 174 to which rechargeable battery 148 is connected through fuse 176. The charge voltage for the battery 148 from the AC power source, is set by resistors 178 and 180. Charging current from the AC output of the transformer 162 to the battery 148 is controlled through a current charging regulator formed by transistor 184, and resistors 186 and 188. Battery charging current will accordingly flow through resistor 188 and when it reaches a predetermined level will turn on transistor 184 to which the negative terminal of the battery is connected by resistor 186. When turned on, the transistor 184 will connect the adjust terminal of the regulator 172 to ground causing it to deliver current at a constant rate to battery 148 for charging purposes. Such charging current will be filtered by capacitor 190.

The main battery bus 174 is also connected to a switching regulator consisting of resistors 192 and 194, regulator circuit chip 196, resistors 198 and 200, transistor 202, inductor 204, diode 206, capacitor 208, resistors 210 and 212 and capacitor 214. The foregoing switching regulator configuration will provide a low level regulated 5-volt DC power supply at terminal 215 for the various components of the control system. A higher level 12-volt DC supply at terminal 217 is also made available by means of a voltage regulator formed by resistors 216, 218 and 220, regulator chip 222, capacitor 224, inductor 226, transistor 228, diode 230, voltage dividing resistors 232 and 234, and filter capacitor 236.

A load test circuit is provided for the battery 148 by means of series connected transistors 238 connected to the positive terminal of the main battery through resistor 240. The input base of the transistors 238 is connected to a load test terminal 242 through capacitor 244 and maintained above ground level by a diode 246.

When power is present from the AC source 146, current controlling device 248 is turned on by current supplied to its input electrode from the output of the AC power transformer 162 through diode 250 and voltage dividing resistor 252 connected in series with grounded voltage dividing resistor 254 and in parallel with capacitor 256. The input to the current controlling device 248 is limited by a grounded Zener diode 258. When conducting, the current controlling device 248 connected to the regulator 172 through resistor 180 will turn it on.

The two-level DC voltage regulator circuits described, to which the unregulated DC voltage bus 174 is connected, will be turned on by the AC source through a power switching control transistor 260, the output collector of which is connected to the ground terminals of the regulator circuit chips 196 and 222. Transistor 260 is turned on by closing of a power switch 262 connected by resistor 264 and inverter 266 to the input terminal of a flip flop 268. The output of the flip flop 268 is connected by inverter 270 and diode 272 to the base of transistor 274. The transistor 274 is accordingly switched on upon closing of switch 262 to connect the unregulated DC voltage bus 174 to the base of transistor 260 causing it to switch on. Switch-on bias for the transistor 274 is established upon closing of the power switch 262 if AC voltage is present. The base of transistor 274 is connected to the AC source by means of series connected inverters 276 and 278 and diode 280. The switching transistor 274 is connected to the base of transistor 260 through voltage reducing resistor 282.

Series connected standby batteries 284 and 286 are also provided as shown in FIG. 8 interconnected between ground and the unregulated DC voltage bus 174 through Zener diode 288 and diode 290. The junction between Zener diode 288 and diode 290 supplies a DC voltage through line 291 to certain components of the control system including a bias voltage to the input side of the inverter 266 through resistor 292. Also, such voltage is supplied to the collector of transistor 294 in order to supply backup voltages from its emitter to other portions of the control system such as the external data memory of the main data processor 124 and its clock calendar circuit. Also, a standby 5-volt DC supply is provided through a Schottky diode 296.

Figure 9:
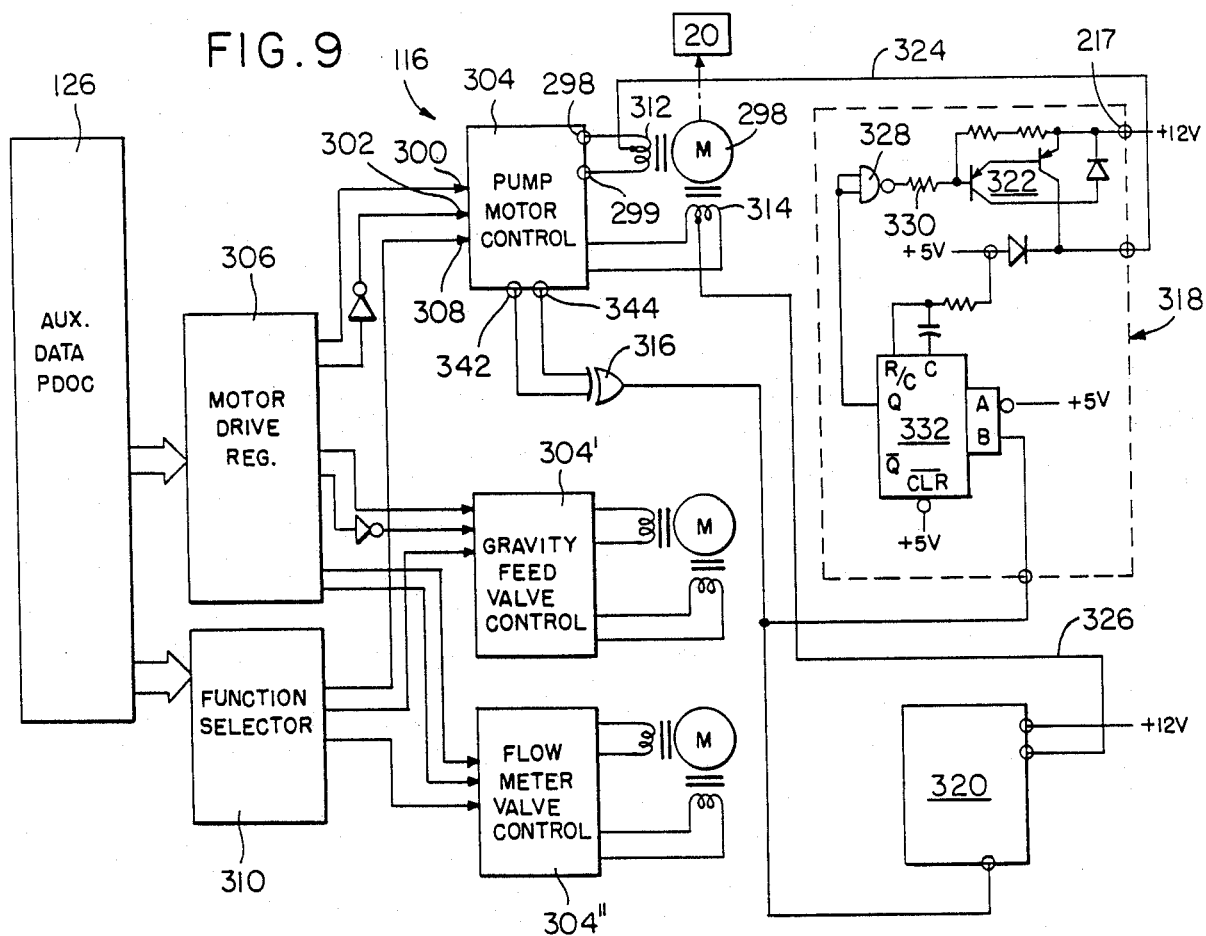
FIG. 9 is an electrical circuit diagram illustrating in greater detail the pump motor controller associated with the electronic control system and its interfacing with the auxiliary data processor.

FIG. 9 illustrates the pump speed controller 116 in greater detail. As shown, the pump 20 is driven by a stepping motor 298 to which directional and enable signals are supplied through terminals 300 and 302 of its motor control circuit 304 by interfacing with the auxiliary data processor 126 through a register 306. Clock terminal 308 of the motor control circuit 304 is also interfaced with the auxiliary data processor through a function selecting decoder 310 for supply of operational signals to the pump motor control circuit 304.

The register 306 and decoder 310 also control the motor circuits 304' and 304" for the controllers 118 and 110. The pump motor 298 is stepped about its rotational axis by a pair of coils 312 and 314 to which drive current is supplied by the motor control circuit. When the control circuit is enabled, a signal output of gate 316 connected to the gate terminals of the motor control circuit 60 also enables a pair of pulse generators 318 and 320 to which the output of gate 316 is connected in parallel. Such generators 318 and 320 are connected to center taps of the driver coils 312 and 314 for step control of the motor. Each pulse generator 318 and 320 includes a current controller 322 connected to the higher level DC voltage supply 217 (+12 volts). The outputs of the current controllers are connected to the drive coil center taps through control lines 324 and 326. The drive current is in the form of pulses determined by the logic output of a NAND gate 328 coupled by a resistor 330 to the current controller 322. The input to the NAND gate 328 is derived from a flip flop 332 as illustrated with respect to the pulse generator driver section 318 in FIG. 9, to which the output of gate 316 is connected.

Figure 10:
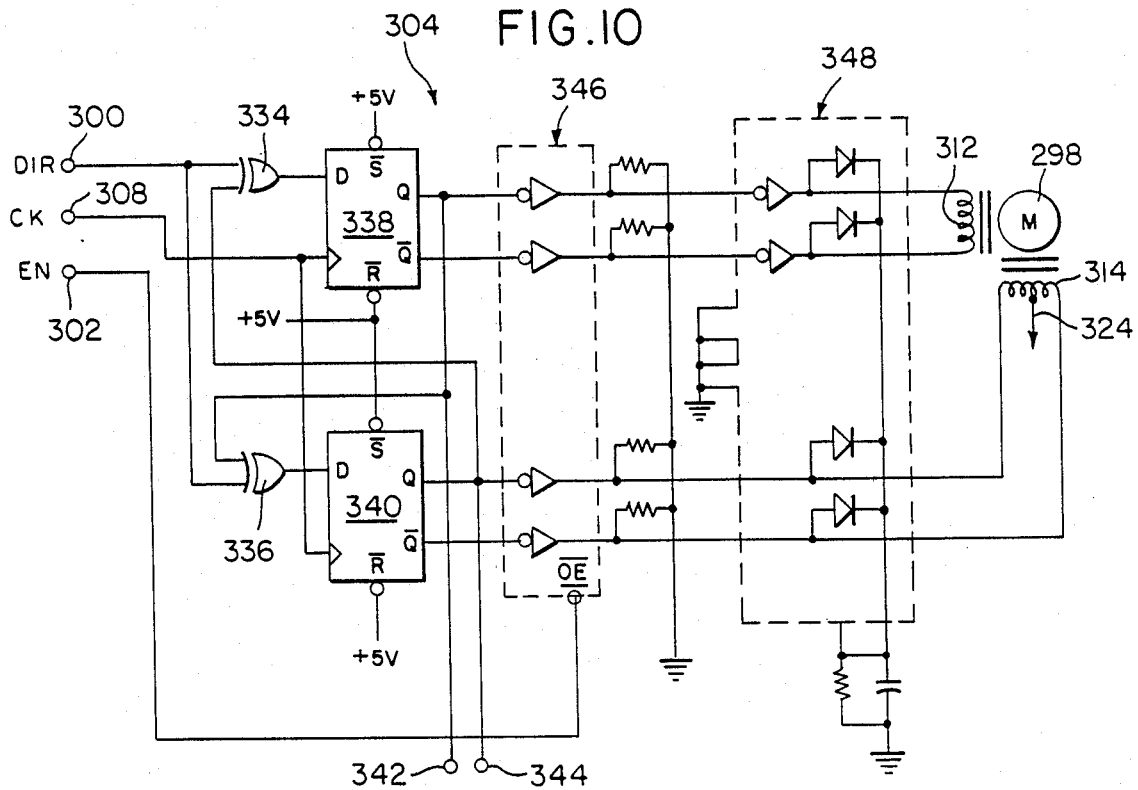
FIG. 10 is an electrical circuit diagram illustrating in greater detail the motor control circuit associated with the controller shown in FIG. 9.

The motor control circuit 304 is illustrated in detail in FIG. 10 showing the directional input terminal 300 connected to one of the inputs of each of the gates 336 and 336. The outputs of the gates 334 and 336 are respectively connected to the drive terminals of a pair of flip flops 338 and 340 from which switching outputs are obtained. The output 342 of flip flop 338 is connected to one of the inputs of gate 316, aforementioned in connection with FIG. 9, and to the input of gate 336. The output 344 of flip flop 340 is connected to the other input of gate 316 and to an input of gate 334. As a result, the switching outputs of the flip flops 338 and 340 are synchronized with each other and fed through gate assemblies 346 and 348 to the drive coils 312 and 314 of the pump motor 298. The motor control circuits 304' and 304" are similar to control circuit 304, without center tap step control to operate the variable flow controller 118 and flow meter valve controller 110.

Figure 13:
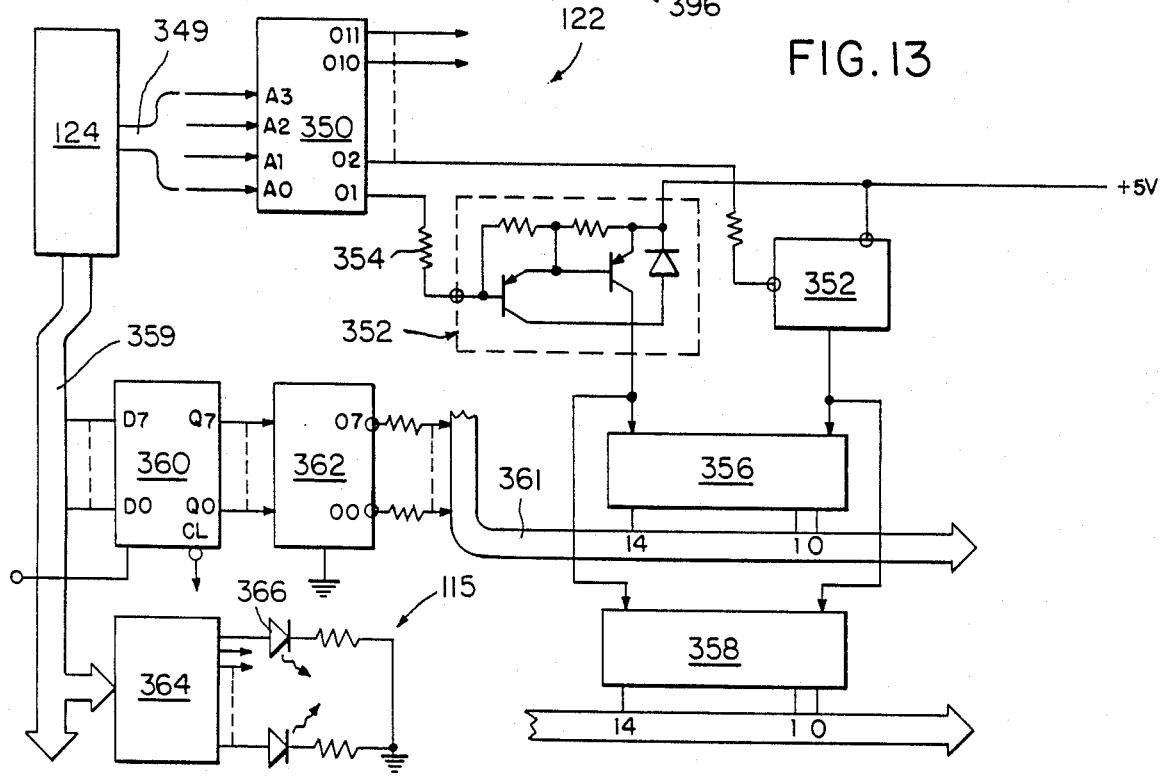
FIG. 13 is an electrical circuit diagram illustrating in detail the display section together with its interfacing to the main data processor.

FIG. 13 illustrates in greater detail the display section 122 as referred to hereinbefore with respect to FIG. 4. The display circuit section includes a display column address decoder 350 interfaced for example with the main data processor 124 through four-bit address bus 349. Ten display column address drivers 352 are respectively coupled by resistors 354 to the outputs of the address decoder 350. A different pair of adjacent drivers 352 are connected to five upper row display units 356 and to five lower row display units 358. These display units may be of the 15 segment type. The upper and lower row display units are respectively connected to segment driver buses 361. Each segment driver bus is connected to an output signal bus 359 of the main data processor 124 through a row segment latch 360 and a row segment driver 362. The bus 359 is also connected to the inputs of a status indicator latch and driver 364 having a plurality of outputs respectively connected to the status indicator 115 in the form of light emitting diodes 366.

Figure 12:
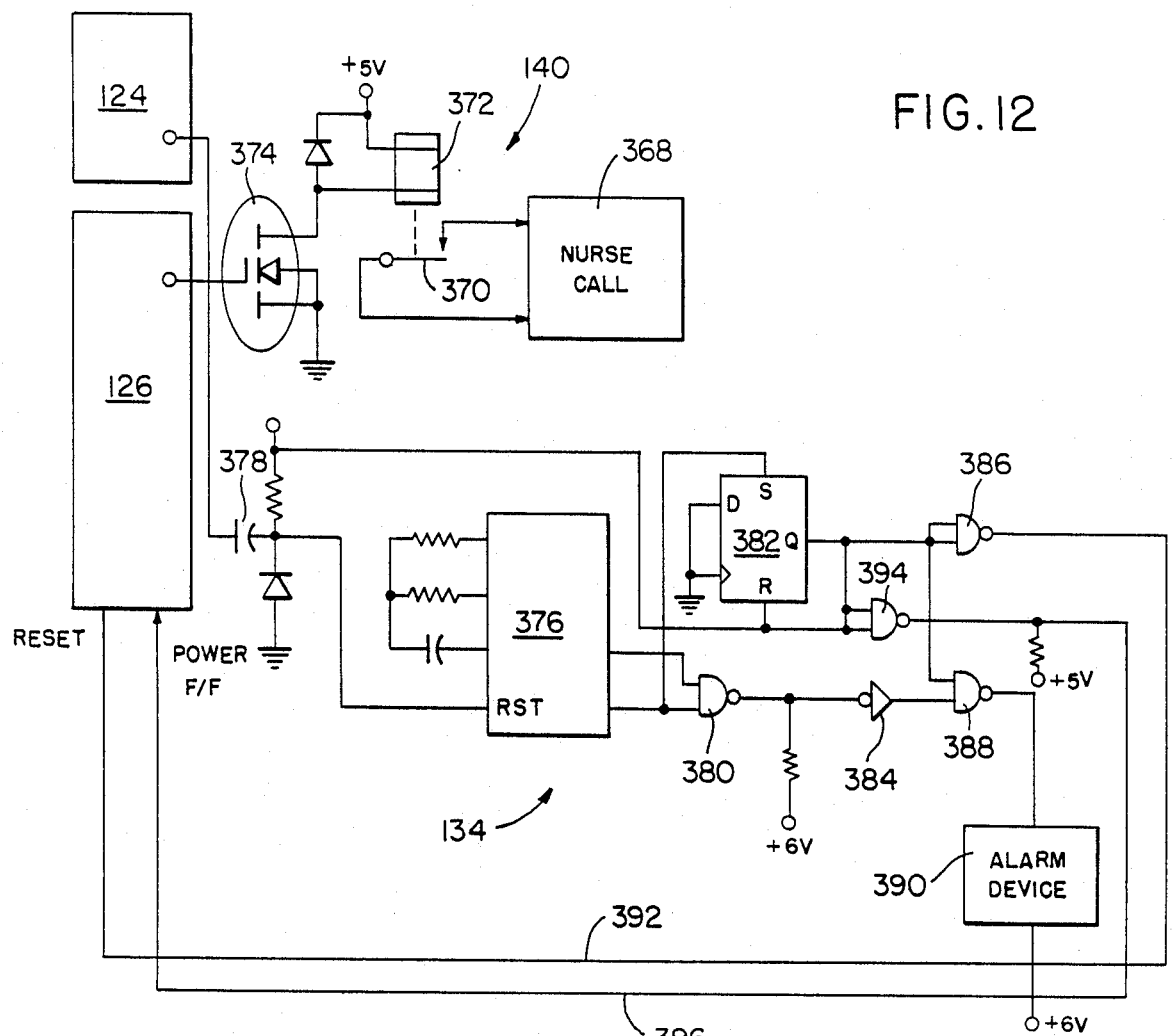
FIG. 12 is an electrical circuit diagram illustrating in detail the nurse call and alarm device together with their interfacing with the auxiliary data processor.

FIG. 12 illustrates in greater detail the nurse calling section 140 which includes an alerting device 368 adapted to be energized or triggered into operation upon closing of a relay switch 370. The relay switch is closed in response to energization of its relay coil 372 when current controlling device 374 completes a ground circuit upon application of an electrode switch-on signal thereto from the auxiliary data processor 126.

The alarm circuit 134 shown in FIG. 12 includes a failure timer chip 376 having its reset terminal connected by capacitor 378 to the main data processor 124. Thus, during normal operation the timer 376 is periodically reset by the main data processor. In the event of failure of the data processor, the pulse input therefrom to the reset terminal of timer 376 stops, causing the timer to count up to a point at which high level outputs are applied to a NAND gate 380, one of such inputs being connected to the set terminal of a error flip flop 382. As a result, a low logic input is applied to inverter 384 from the NAND gate 380. The high logic output from the set flip flop 382 is then applied to the NAND gate 386 and the NAND gate 388. Since the NAND gate 388 has one of its inputs connected to the output of inverter 384, it will produce a low logic trigger output applied to alarm device 390. At the same time, the logic output of NAND gate 386 generates a reset signal fed through reset line 392 to the data processor 126 in order to clear various latches therein. A NAND gate 394 also connected to the output of flip flop 384, generates a power status signal applied to the data processor 126 through signal line 396.

Figure 11:
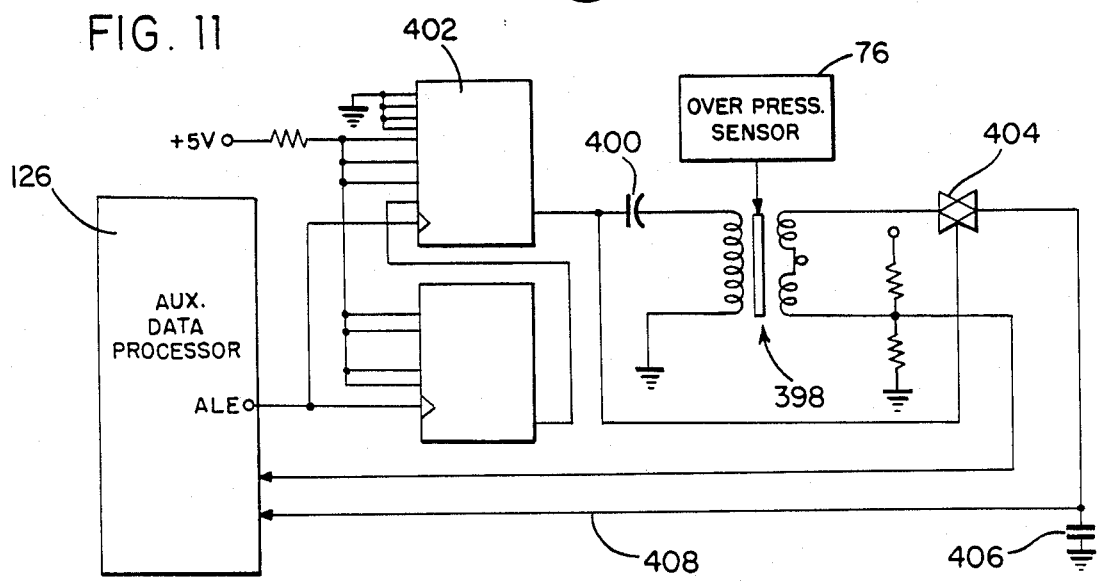
FIG. 11 is an electrical circuit diagram illustrating in greater detail the over pressure detector as schematically depicted in FIGS. 3 and 4 interfaced with the auxiliary data processor.

FIG. 11 illustrates the interfacing of the over-pressure sensor 76 with the auxiliary data processor 126 through a linear variable differential transformer 398. Displacement of the pressure sensing diaphragm of sensor 76 is transmitted to the transformer 398 through which such displacement is measured. A drive signal is fed to the primary winding of the transformer through capacitor 400 from a driver circuit chip 402 to which a drive signal is supplied from the data processor 126. The output winding of the transformer 398 is connected to a detector 404 through which a capacitor 406 is charged to a voltage level which represents the fluid pressure within the tubing of the cassette 36 downstream of the pump 20. The voltage to which the capacitor 406 is charged is fed to the data processor through signal line 408.

It should be understood that various other changes and modifications may be resorted to without departing from the spirit and scope of the invention as defined in the appended claims.

What is claimed is:

1. In a flow control system through which fluid is delivered to an outlet conduit, flow metering means for monitoring flow of the fluid delivered to said outlet conduit, a plurality of reservoirs from which the fluid is withdrawn, a fluid displacement pump, flow passage means connected to the reservoirs and the pump for establishing flow of the fluid between the reservoirs and the flow metering through the pump, and in bypass relation thereto and mode control means operatively connected to the flow passage means for selectively conducting the said flow of fluid therethrough alternatively and simultaneously under a gravity head from the reservoirs and from the pump under a positive pressure head to the metering means.

2. The system as defined in claim 1 wherein the mode control means includes a variable flow valve downstream of the reservoirs interconnecting the reservoirs and the metering means in parallel with the pump, means for maintaining the flow valve closed during an exclusive pump mode of operation, and means for rendering the flow control valve operative to vary flow therethrough under said gravity head and during modes of operation involving flow under both the gravity head and the positive pressure head.

3. The system as defined in claim 2, including selector means connected to the flow passage means for limiting withdrawal of the fluid under the gravity head from one of the reservoirs.

4. In a flow control system through which fluid is delivered to an outlet conduit, a plurality of reservoirs from which the fluid is withdrawn, a fluid displacement pump, flow passage means connected to the reservoirs and the pump for establishing fluid communication between the reservoirs and the pump, mode control means operatively connected to the flow passage means for conducting the fluid therethrough under a gravity head from the reservoirs and from the pump under a positive pressure head, flow metering means for monitoring flow of the fluid delivered to said outlet conduit including, pressure sealed chamber means for receiving the fluid from said flow passage means, piston means displaceable between limit positions within the chamber means for displacing the fluid therefrom, flow directing valve means operatively connected to the chamber means and establishing different flow paths along which the fluid is conducted to and from the chamber means for displacement of the piston means, operational control means operatively connected to the flow directing valve means and responsive to the piston means reaching the limit position thereof for changing the flow paths to effect a reversal in travel of the piston means, sensing means for measuring said displacement of the piston means with respect to time, and means operatively connected to the sensing means for calculating flow rate of the fluid as a function of said measurement of the displacement of the piston means, the mode control means including a variable flow valve connected by the flow passage means downstream of the reservoirs between the reservoirs and the metering means in parallel with the pump, means for maintaining the flow valve closed during a pump mode of operation, and means for rendering the flow control valve operative during a mode of operation involving gravity feed.

5. The combination of claim 4, including selector means connected to the flow passage means for selectively limiting withdrawal of the fluid under the gravity head from one of the reservoirs.

6. In a flow control system for administration of intravenous fluid having reservoir means from which the fluid is withdrawn and an infusion conduit to which the fluid is delivered at a selected flow rate, a fluid displacement pump, flow passage means connected to the reservoir means and the pump for conducting the fluid to the infusion conduit, flow metering means connected to the flow passage means for monitoring flow of the fluid delivered to the infusion conduit to generate flow data, variable flow means in the flow passage means for conducting the fluid to the infusion conduit in bypass relation to the pump under a gravity head, and programmed control means responsive to the flow data generated by the flow metering means for regulating operation of the pump and the variable flow means to maintain the fluid delivered to the infusion conduit at said selected flow rate.

7. The improvement as defined in claim 6, wherein said reservoir means includes a plurality of fluid reservoirs and selector means connected to the flow passage means for selectively limiting withdrawal of the fluid under the gravity head from one of the reservoirs.

8. The improvement as defined in claim 6, wherein the flow metering means includes pressure sealed chamber means for receiving the fluid from the reservoir means, piston means displaceable between limit positions within the chamber means for displacing the fluid therefrom, flow directing valve means operatively connected to the chamber means and establishing different flow paths along which the pressurized fluid is conducted to and from the chamber means for displacement of the piston means, operational control means connected to the flow directing valve means and responsive to the piston means reaching the limit positions thereof for reversing travel of the piston means, sensing means for measuring said displacement of the piston means with respect to time and means operatively connected to the sensing means for calculating flow rate of the fluid as a function of said measurement of the displacement of the piston means.

9. In combination with a system for infusion of fluid from at least two sources, having an infusion conduit, pump means for displacing the fluid to the infusion conduit under a positive pressure, flow controlling valve means for conducting the fluid to the infusion conduit by gravity feed, flow metering means for measuring volumetric flow of the fluid to the infusion conduit, operational means connected to the pump means and the flow controlling valve means for respectively varying flow of the fluid under said positive pressure and gravity feed, data processing means connected to the flow metering means for establishing a preselected flow rate at which the fluid is delivered to the infusion conduit, and programmed means interfacing the data processing means with the operational means for adjustment of said varying flow through the pump means and the flow controlling valve means to maintain the fluid conducted to the infusion conduit at the preselected flow rate.

10. The combination of claim 9, including feed control means connected to the sources and the programmed means for selecting flow of the fluid at said preselected flow rate from one or more of the sources.

11. A method of administering intravenous fluid through an infusion device, including the steps of: selecting a volumetric flow rate at which the fluid is to be delivered to the infusion device; establishing parallel flow paths along which flow of the fluid is respectively induced by gravity and positive pump displacement; selecting the flow path along which the fluid is delivered to the infusion device; measuring the actual flow rate of the fluid delivered to the infusion device; and adjusting said flow of the fluid respectively induced by gravity and positive pump displacement in accordance with the measured flow rate to substantially maintain the delivery of the fluid at said selected flow rate.

12. The method of claim 11, wherein said fluid is adapted to be withdrawn from at least two reservoirs; and including the step of: selecting the reservoir from which the fluid is withdrawn.

13. The method of claim 12, wherein said step of adjusting the flow includes comparing the measured flow rate with the selected flow rate; and varying flow along the selected flow path as a function of the differential between the measured and selected flow rates.

14. The method of claim 11, wherein said step of adjusting the flow includes comparing the measured flow rate with the selected flow rate; and varying flow along the selected flow path as a function of the differential between the measured and selected flow rates.

* * * * *